(12) United States Patent
Voic

(10) Patent No.: US 10,675,052 B2
(45) Date of Patent: *Jun. 9, 2020

(54) ULTRASONIC WOUND TREATMENT APPARATUS AND ASSOCIATED METHOD

(71) Applicant: MISONIX, INCORPORATED, Farmingdale, NY (US)

(72) Inventor: Dan Voic, Cedar Grove, NJ (US)

(73) Assignee: MISONIX, INCORPORATED, Farmingdale, NY (US)

(*) Notice: Subject to any disclaimer, the term of this patent is extended or adjusted under 35 U.S.C. 154(b) by 241 days.

This patent is subject to a terminal disclaimer.

(21) Appl. No.: 15/873,607

(22) Filed: Jan. 17, 2018

(65) Prior Publication Data

US 2018/0214174 A1 Aug. 2, 2018

Related U.S. Application Data

(63) Continuation of application No. 14/797,660, filed on Jul. 13, 2015, now Pat. No. 9,872,697.

(51) Int. Cl.
*A61B 17/32* (2006.01)
*A61N 7/00* (2006.01)
*A61B 17/00* (2006.01)

(52) U.S. Cl.
CPC ........ *A61B 17/320068* (2013.01); *A61N 7/00* (2013.01); *A61B 2017/00761* (2013.01); *A61B 2017/320008* (2013.01); *A61B 2017/320072* (2013.01); *A61B 2217/007* (2013.01); *A61N 2007/0017* (2013.01); *A61N 2007/0034* (2013.01)

(58) Field of Classification Search
CPC ........ A61B 17/320068; A61B 17/3207; A61B 17/54; A61B 2017/320024; A61B 2017/320072; A61B 2017/320008
See application file for complete search history.

(56) References Cited

U.S. PATENT DOCUMENTS

| | | | |
|---|---|---|---|
| 7,431,704 B2 | 10/2008 | Babaev | A61B 17/320068 239/102.2 |
| 8,512,340 B2 | 8/2013 | Easley et al. | |
| 2007/0149881 A1 | 6/2007 | Rabin | A61B 17/32002 600/471 |
| 2008/0058775 A1 | 3/2008 | Darian et al. | |
| 2008/0139995 A1 | 6/2008 | Guerra | |
| 2009/0312692 A1 | 12/2009 | Cotter et al. | |
| 2010/0167235 A1 | 7/2010 | Vercellotti et al. | |
| 2011/0196399 A1 | 8/2011 | Robertson | A61B 17/22004 606/169 |
| 2012/0101512 A1 | 4/2012 | Locke et al. | |

FOREIGN PATENT DOCUMENTS

CN 1043368246 2/2015

*Primary Examiner* — Ashley L Fishback
(74) *Attorney, Agent, or Firm* — R. Neil Sudol; Henry D. Coleman

(57) ABSTRACT

An ultrasonic medical treatment probe has a head with a distal-most circular rim extending along an endless uninterrupted perimeter around a broad recess and formed with a series of serrations or teeth. The rim is thin in comparison to the width of the recess. The serrations or teeth preferably extend continuously along an entire circumference or length of the rim. The probe head is provided along the rim with a plurality of notches or openings communicating with the recess.

15 Claims, 1 Drawing Sheet

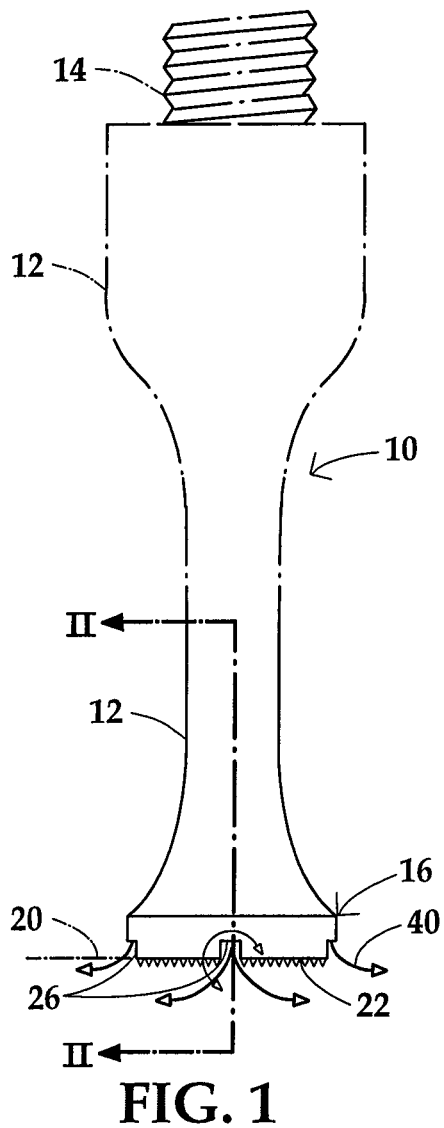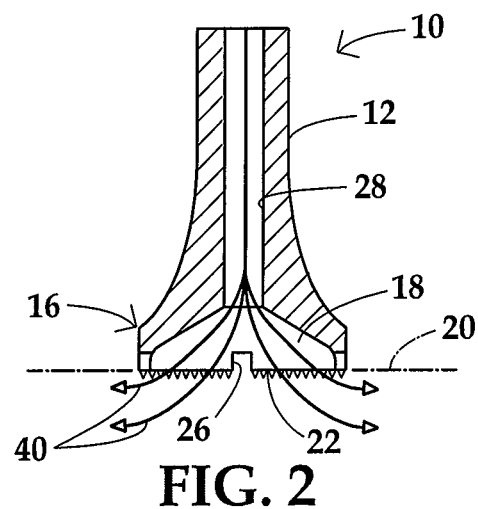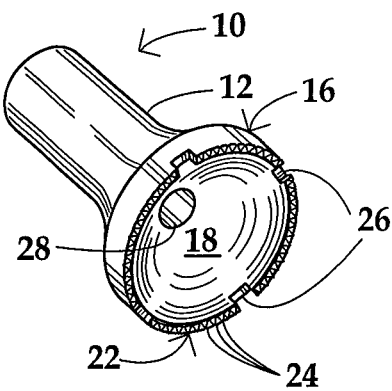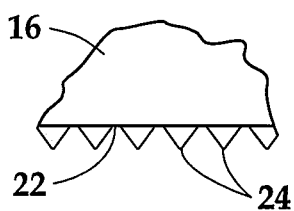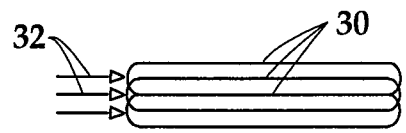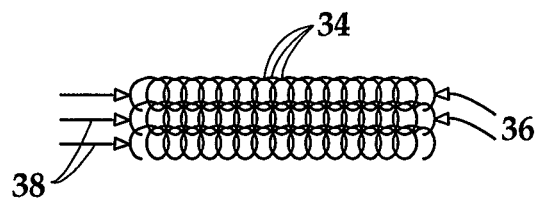

ULTRASONIC WOUND TREATMENT APPARATUS AND ASSOCIATED METHOD

CROSS-REFERENCE TO RELATED APPLICATION

This application is a continuation of U.S. patent application Ser. No. 14/797,660 filed Jul. 13, 2015, now U.S. Pat. No. 9,872,697.

BACKGROUND OF THE INVENTION

This invention relates to ultrasonic surgical instruments and associated methods of use. More particularly, this invention relates to the treatment of wounds with ultrasound energy. The treatment contemplated by this invention includes fragmentation and emulsification of hard and soft tissue in a clinical environment while reducing unwanted heat and collateral tissue damage.

Over the past 30 years, several ultrasonic tools have been invented which can be used to ablate or cut tissue in surgery. Such devices are disclosed by Wuchinich et al. in U.S. Pat. No. 4,223,676 and Idemoto et al in U.S. Pat. No. 5,188,102.

In practice, these surgical devices include a blunt tip hollow probe that vibrates at frequencies between 20 kc and 100 kc, with amplitudes up to 300 microns or more. Such devices ablate tissue by either producing cavitation bubbles which implode and disrupt cells, by generating tissue compression and relaxation stresses (sometimes called the jackhammer effect) or by other mechanisms such as micro streaming of bubbles in the tissue matrix. The effect is that the tissue becomes liquefied and separated. The fragmented tissue becomes emulsified with an irrigant solution. The resulting emulsion or slurry of tissue debris is then aspirated from the site. Bulk excision of tissue is possible by applying the energy around and under an unwanted tissue mass to separate it from the surrounding structure. The surgeon can then lift the separated tissue mass out using common tools such as forceps.

The tubular probe is excited by a transducer of either the piezoelectric or magnetostrictive type that transforms an alternating electrical signal within the frequencies indicated above into a longitudinal or transverse vibration. When the probe is attached to the transducer, the two become a single element with series and parallel resonances. The designer will try to tailor the mechanical and electrical characteristics of these elements to provide the proper frequency of operation. Most of the time, the elements will have a long axis that is straight and has the tip truncated in a plane perpendicular to the long axis. This is done for simplicity and economic considerations. In almost all applications, whether medical or industrial, such an embodiment is practical and useful. However, in applications such as the debridement of burns, wounds, diabetic ulcers or ulcers induced by radiation treatments, the blunt straight probe has been shown to be less effective in removing the hard eschar buildup that occurs when the wound is healing. This eschar buildup must be removed so that the healthy tissue is exposed and allowed to close the wound to provide complete healing with minimal scar tissue formation. Also, the small diameter tip, since it is cannulated, has a small annular area with limits energy transmission into the wound. This extends the length of the procedure and causes operator fatigue and patient discomfort.

Therefore, it was desired to provide a probe that can be mated to an ultrasonic surgical aspirator that increases the efficiency of emulsification, does not heat up the operative site and lowers the time of operation.

In response to this need, a series of devices were developed which have been proven to address at least some of the shortcomings of the previous techniques. These devices are described in U.S. Pat. No. 7,931,611 issued Apr. 26, 2011. The devices have been shown to be effective in clinical use for the removal of necrotic tissue and some softer types of eschar.

High temperature burns produce a tough, leathery type of eschar. While the eschar can slough off naturally, its removal through surgical debridement is often necessary in order to prevent infection. This is even more important for immunocompromised patients. A frequently used eschar removal option involves the use of a manual dermatome such as a Weck knife. The surgeon cuts thin slices of eschar until the healthy tissue is exposed. Bleeding is the key visual indicator when the Weck knife has reached healthy tissue. Ideally, the eschar should be removed without any insult to the healthy tissue below. As this is not possible, the thinner the layer of healthy tissue removed during debridement, the more successful the eschar removal procedure.

The ultrasonic debridement of wounds, as described above, has already been proven as an extremely precise, necrotic tissue removal method with the added benefit of minimum impact to the healthy tissue. Ultrasound wound debridement probes are used for debriding complex tissue topographies with minimal loss of healthy tissue. This is not possible to duplicate with sharps, such as scalpels or Weck knives.

Because some of the mechanical properties of the high temperature-induced eschar, such as elasticity, are close to those of healthy tissue, ultrasonic debridement using the ultrasonic debridement tools developed to date is problematic.

OBJECTS OF THE INVENTION

An object of the present invention is to provide an improved ultrasonic surgical instrument for use in wound treatment.

A more particular object of the present invention is to provide such an instrument that will improve wound healing times.

Another particular object of the present invention is to provide such an instrument that may be used in the debridement of wounds that evince a tough, leathery type of eschar.

It is a further object of the present invention to provide such an improved ultrasonic surgical instrument that is easy to use.

It is an associated object of the present invention to provide an improved method of debridement of wounds, such as high temperature burns exhibiting a tough, leathery type of eschar.

These and other objects of the invention will be apparent from the drawings and descriptions herein. Although every object of the invention is attained in at least one embodiment of the invention, there is not necessarily any embodiment which attains all of the objects of the invention.

SUMMARY OF THE INVENTION

An ultrasonic medical treatment probe in accordance with the present invention comprises a shaft or shank, a connector and a probe head. The connector, disposed at one end of the shaft or shank, is configured for coupling to a source of ultrasonic vibratory energy. The probe head is located at an end of the shaft or shank opposite the connector and includes a recess opening onto a distal end plane of the instrument. The probe head has a distal-most rim extending along an endless uninterrupted perimeter around the recess and is formed with a series of serrations or teeth.

Pursuant to the present invention, the distal-most rim is disposed in a plane, exemplarily, but not necessarily, oriented at a 90° angle relative to an axis of the shaft.

Preferably, the rim is circular, the probe head has a cup-shaped configuration, and the rim constitutes an edge of the probe head. As in any typical cup shape, the rim is thin in comparison to the width of the recess. While the rim is no thicker than a few millimeters, the recess is typically 5-15 millimeters in diameter. Thus, the diameter of the recess is roughly an order of magnitude larger than the width of the rim.

The serrations or teeth preferably extend continuously along an entire circumference of the rim. The resulting symmetry facilitates use of the device to debride a wound surface. The entire geometry of the probe head is particularly conducive to effective removal of eschar from tissue surfaces having high-temperature burns.

Pursuant to another feature of the present invention, the probe head is provided along the rim with a plurality of notches or openings communicating with the recess. Preferably, the probe head is provided along the rim with exactly four notches or openings communicating with the recess.

A wound debridement method in accordance with the present invention utilizes an ultrasonic probe having a shaft or shank, a connector at one end of the shaft or shaft configured for coupling to a source of ultrasonic vibratory energy, and a probe head at an end of the shaft or shank opposite the connector, the probe head including a recess opening onto a distal end plane, the probe head having a distal-most rim extending along an endless uninterrupted perimeter around the recess, the rim being formed with a series of serrations or teeth. The method comprises placing the rim including the serrations or teeth in contact with a target surface of a patient, moving the probe so that the rim moves in a predetermined pattern parallel to and along the target surface while the rim including the serrations or teeth is in contact with the surface, and, during the moving of the probe, generating an ultrasonic standing wave in the probe to vibrate the rim and thereby debride the target surface. Preferably, liquid is conducted through a channel or bore in the probe shaft to the recess in the probe head during the moving of the probe in contact with the target surface.

The predetermined pattern of probe motion may be a series of parallel passes adjacent to and preferably overlapping slightly to ensure removal of a continuous layer of eschar at a burn site. The same result may be achieved by moving the probe in a series of overlapping loops. The loops may be roughly circular and the overlapping circles may be disposed in a linear arrangement to generate a rectangular swath of debrided tissue surface. Again, several passes of looping probe movements may be undertaken to debride a wide area. In general, the moving of the probe is such that the serrated rim is moved laterally within a plane constituting at least a portion of the target surface.

It is contemplated that the serrated rim of the probe head is vibrated at velocities of 10 to 18 m/s RMS. A combination of frequency-amplitude operational parameters may be selected to ensure such velocities. For example, for 22.5 KHz the output amplitude range that produces the desired speed interval of 10-18 m/s RMS is 200-360 um.

BRIEF DESCRIPTION OF THE DRAWINGS

FIG. 1 is a side elevational view, partially schematized, of an ultrasonic wound debridement probe in accordance with the present invention, showing a serrated distal edge.

FIG. 2 is a partial longitudinal cross-sectional view taken along line II-II in FIG. 1.

FIG. 3 is a perspective view of the probe of FIGS. 1 and 2.

FIG. 4 is a partial side elevational view, on an enlarged scale, of the distal edge of the probe of FIGS. 1-3.

FIG. 5 is a diagram showing a pattern of use of the probe of FIGS. 1-4.

FIG. 6 is a diagram showing an alternative pattern of use of the probe of FIGS. 1-4.

DETAILED DESCRIPTION

As illustrated in FIGS. 1-3, an ultrasonic medical treatment probe 10 comprises a shaft or shank 12, a connector 14, and a probe head 16. Connector 14, disposed at one end of shaft or shank 12, is configured for coupling to a source of ultrasonic vibratory energy. Probe head 16 is located at an end of shaft or shank 12 opposite the connector 14 and is transversely enlarged so as to define a large recess 18 opening onto a distal end plane 20 of the instrument. Probe head 16 has a distal-most rim 22 extending along an endless uninterrupted perimeter around recess 18 and is formed with a series of serrations or teeth 24 pointed or tapering in a distal direction.

Distal-most rim 22 is disposed in plane 20 that is, exemplarily, but not necessarily, oriented at a 90° angle relative to an axis of shaft 12.

Preferably, rim 12 is circular, probe head 16 has a cup-shaped configuration, and rim 22 constitutes an edge of the probe head. As in any typical cup shape, rim 22 is thin in comparison to the width of recess 18. While the rim 22 is no thicker than a few millimeters, the recess is typically at least 5-15 millimeters in diameter. Thus, the diameter of recess 18 is roughly an order of magnitude larger than the width of rim 22.

Serrations or teeth 24 preferably extend continuously along an entire circumference of rim 22. The resulting symmetry facilitates use of the device 10 to debride a wound surface. The entire geometry of probe head 16 is particularly conducive to effective removal of eschar from tissue surfaces having high-temperature burns.

Probe head 16 is preferably provided along rim 22 with a plurality of mutually spaced notches or openings 26 communicating with recess 18. As illustrated, probe head 16 is provided along rim 22 with exactly four notches or openings 26 communicating with recess 18. Notches or openings 26 are substantially larger than serrations or teeth 24. Serrations or teeth 24 extend continuously along rim or edge 22 between notches or openings 26. Serrations or teeth 24 are spaced from one another by gaps (not separately enumerated) substantially smaller than notches or openings 26. Notches or openings 26 extend a first distance along rim or edge 22, while serrations or teeth 24 each extend a second distance along the rim or edge, the first distance being more than two times the second distance.

Shaft or shank 12 is formed with a central channel or bore 28 that communicates at a distal end with recess 18 and penetrates at a proximal end through connector 14 for communicating via a handpiece (not shown) with a pressurized source of irrigation liquid. The irrigation liquid is typically a saline solution that may have antibiotic and/or anesthetic constituents.

A wound debridement method utilizing probe 10 entails manipulating the probe to place rim 22 including serrations or teeth 24 in contact with a target surface of a patient, and moving the probe so that the rim moves in a predetermined pattern parallel to and along the target tissue surface while the rim including the serrations or teeth is in contact with the tissue surface. During the moving of probe 10, one generates an ultrasonic standing wave in the probe to vibrate rim 22 and the serrations or teeth 24 thereof, thereby debriding the target surface. Irrigation liquid is conducted through channel or bore 28 in probe shaft 12 to recess 18 in probe head 16 and out through notches 26 (as indicated by arrows 40) during the moving of the probe 10 in contact with the target surface.

One pattern of probe motion, depicted in FIG. 5, is a series of parallel passes 30 adjacent to each other and preferably overlapping slightly to thereby ensure removal of a continuous or uninterrupted layer of eschar at a burn site. The parallel passes 30 may be separate, that is, temporally spaced owing to a lifting of the probe 10 away from the target skin surface and a repositioning of the probe prior to motion in the same direction as indicated by arrows 32. Alternatively, alternate passes 30 may be in an opposite direction, with the probe remaining on the target skin surface during the changes in direction of probe motion.

Another pattern of probe motion, shown in FIG. 6, is a series of overlapping loops 34. The loops 34 are roughly circular and the overlapping circles may be distributed in arrays 36 to generate linear passes each clearing a rectangular swath or path of debrided tissue surface. Again, several debridement passes 36 of looping probe movement may be undertaken to debride a wide area. The parallel passes 36 may be separate, that is, temporally spaced owing to a lifting of the probe 10 away from the target skin surface and a repositioning of the probe prior to motion in the same direction as indicated by arrows 38. Alternatively, alternate looping passes 36 may be in an opposite direction, with the probe remaining on the target skin surface during the changes in direction of probe motion.

In general, the moving of probe 10 is such that the serrated rim is moved laterally within a plane constituting at least a portion of the target surface.

It is contemplated that the serrated rim of the probe head is vibrated at velocities of 10 to 18 m/s RMS. A combination of frequency-amplitude operational parameters may be selected to ensure such velocities. For example, for 22.5 KHz the output amplitude range that produces the desired speed interval of 10-18 m/s RMS is 200-360 um.

Probe 10 and the use thereof in wound debridement combines the following parameters at the probe-tissue interface: (1) high contact pressure, (2) high velocities of rim 22 and teeth 24, and (3) irrigation via channel 28 and recess 18. Probe 10 has proven highly efficient in the precise and efficient removal of tough, leathery type of eschar produced by high temperature burns. Key elements of probe 10 include an annular contact area fitted with serrated edge 22 to ensure a high contact pressure, needed for tissue penetration and disruption, at the probe-tissue interface. Notches 26, set 90° apart around the annular perimeter of the distal end of the instrument head 16, allow irrigant to exit the probe even during full contact with the target tissue.

Again, an optimal operation of probe 10 contemplates a combination of frequency-amplitude operational parameters that ensure high velocities exemplarily between 10 and 18 m/s RMS. Example: for 22.5 KHz the output amplitude range that produces the desired speed interval of 10-18 m/s RMS is 200-360 um.

Although the invention has been described in terms of particular embodiments and applications, one of ordinary skill in the art, in light of this teaching, can generate additional embodiments and modifications without departing from the spirit of or exceeding the scope of the claimed invention. In some applications it may be beneficial if rim 22 has a shape other than circular, for instance, oval or elliptical or oblong with rounded or truncated corners. Accordingly, it is to be understood that the drawings and descriptions herein are proffered by way of example to facilitate comprehension of the invention and should not be construed to limit the scope thereof.

What is claimed is:

1. An ultrasonic medical treatment probe comprising:
   a shaft or shank;
   a source of ultrasonic vibratory energy;
   a connector at one end of said shaft or shaft operatively coupling said shaft or shank to said source of ultrasonic vibratory energy; and
   a probe head at an end of said shaft or shank opposite said connector, said probe head including a recess opening onto a distal end plane, said probe head having a circular distal-most rim or edge extending around said recess, said distal-most rim or edge being formed with a series of serrations or teeth, said distal-most rim or edge being further formed with a plurality of notches or openings communicating with said recess, said notches or openings being substantially larger than said serrations or teeth, said serrations or teeth extending continuously along said distal-most rim or edge between said notches or openings, said serrations or teeth being spaced from one another by gaps substantially smaller than said notches or openings.

2. The probe defined in claim 1 wherein said distal-most rim or edge is disposed in a plane.

3. The probe defined in claim 1 wherein said plane is oriented perpendicularly to an axis of said shaft or shank.

4. The probe defined in claim 1 wherein said probe head has a cup-shaped configuration.

5. The probe defined in claim 1 wherein said probe head is provided along said distal-most rim or edge with exactly four said notches or openings communicating with said recess.

6. The probe defined in claim 1 wherein said serrations or teeth project in a distal direction from said distal-most rim or edge and are disposed only on a side of said distal-most rim or edge facing in said distal direction.

7. The probe defined in claim 1 wherein said notches or openings extend a first distance along said distal-most rim or edge, said serrations or teeth each extending a second distance along said distal-most rim or edge, said first distance being more than two times said second distance.

8. The probe defined in claim 1 wherein a multiplicity of said serrations or teeth are disposed between consecutive or successive ones of said notches or openings along said distal-most rim or edge.

9. A wound debridement method comprising:
   providing an ultrasonic probe having a shaft or shank, a connector at one end of said shaft or shank configured for coupling to a source of ultrasonic vibratory energy, and a probe head at an end of said shaft or shank opposite said connector, said probe head including a recess opening onto a distal end plane, said probe head having a distal-most rim or edge extending around said recess, said distal-most rim or edge being formed with a series of serrations or teeth, said distal-most rim or edge being further formed with a plurality of notches or openings communicating with said recess, said notches or openings being substantially larger than said serrations or teeth, said serrations or teeth extending continuously along said distal-most rim or edge between said notches or openings, said serrations or teeth being spaced from one another by gaps substantially smaller than said notches or openings;

coupling said connector to a source of ultrasonic vibratory energy;

placing said distal-most rim or edge including said serrations or teeth in contact with a target surface of a patient;

moving said probe so that said distal-most rim or edge moves in a predetermined pattern parallel to and along said target surface while said distal-most rim or edge including said serrations or teeth is in contact with said target surface; and during the moving of said probe, generating an ultrasonic standing wave in said probe to vibrate said distal-most rim or edge and thereby debride said target surface.

10. The method defined in claim 9 wherein during the moving of said probe, said distal-most rim or edge is moved laterally within a plane constituting at least a portion of said target surface.

11. The method defined in claim 9 wherein said plane is oriented perpendicularly to an axis of said shaft or shank.

12. The method defined in claim 9 wherein said distal-most rim or edge is vibrated at velocities of 10 to 18 m/s RMS.

13. An ultrasonic medical treatment probe comprising:
a shaft or shank having a longitudinal axis;
a connector at one end of said shaft or shank configured for coupling to a source of ultrasonic vibratory energy; and
a probe head at an end of said shaft or shank opposite said connector, said probe head including a recess opening onto a distal end plane oriented perpendicularly to said longitudinal axis, said probe head having a distal-most rim or edge extending around said recess and in said distal end plane, said distal-most rim or edge being formed with a series of serrations or teeth that point or taper in a distal direction from said distal end plane.

14. The probe defined in claim 13 wherein said distal-most rim or edge is further formed with a plurality of notches or openings communicating with said recess, said notches or openings being substantially larger than said serrations or teeth, a plurality of said serrations or teeth extending along said distal-most rim or edge between consecutive or successive ones of said notches or openings.

15. The probe defined in claim 14 wherein said distal-most rim or edge is circular.

* * * * *